US00PP16985P2

(12) United States Plant Patent
Olesen

(10) Patent No.: US PP16,985 P2
(45) Date of Patent: Aug. 15, 2006

(54) SHRUB ROSE PLANT NAMED 'POULCOT007'

(50) Latin Name: *Rosa* hybrid
Varietal Denomination: Poulcot007

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 49 days.

(21) Appl. No.: 11/090,137

(22) Filed: Mar. 24, 2005

(51) Int. Cl.
*A01H 5/00* (2006.01)

(52) U.S. Cl. ..... Plt./108
(58) Field of Classification Search ..... Plt./108
See application file for complete search history.

*Primary Examiner*—Kent Bell
*Assistant Examiner*—Annette H Para

(57) ABSTRACT

A new garden rose plant of the shrub rose class which has abundant, medium red flowers and attractive foliage. This new and distinct variety has shown to be uniform and stable in the resulting generations from asexual propagation.

3 Drawing Sheets

Botanical designation: *Rosa* hybrid.
Variety denomination: 'Poulcot007'.

SUMMARY OF THE INVENTION

The present invention constitutes a new and distinct variety of garden rose plant that originated from a controlled crossing between the unnamed female seed parent and the unnamed male pollen parent.

The two parents were crossed during the summer of 1995, and the resulting seeds were planted in a controlled environment in Fredensborg, Denmark. The new variety, named 'Poulcot007' was a single plant selection resulting from the stated cross.

The new variety may be distinguished from its female seed parent by the following combination of characteristics:

1. The seed parent has a taller growth habit than 'Poulcot007'.
2. The seed parent has red flowers, while 'Poulcot007' has medium red flowers.

The new variety may be distinguished from its male pollen parent from the following combination of characteristics:

1. The pollen parent has a higher petal count than 'Poulcot007'.
2. The pollen parent produces fewer rose hips than 'Poulcot007'.

The objective of the hybridization of this rose variety was to create a new and distinct variety for garden use with unique qualities, such as:

1. Uniform and abundant medium red flowers;
2. Vigorous, but compact growth when propagated both as a budded rose and on its own roots;
3. Disease resistance;
4. Profuse development of rose hips;
5. Continuous flowering habit.

This combination of qualities is not present in previously available commercial cultivars of this type, known to the inventor, and distinguish 'Poulcot007' from all other varieties of which we are aware.

As part of the rose development program, Mogens N. Olesen germinated the seeds from the aforementioned hybridization during winter of 1995 and conducted evaluations on the resulting seedlings in a controlled environment in Fredensborg, Denmark.

'Poulcot007' was selected in the spring of 1996 by the inventor as a single plant from the progeny of the aforementioned hybridization.

Asexual reproduction of 'Poulcot007' by traditional budding and rooted cuttings was first done by Mogens N. Olesen in the nursery in Fredensborg, Denmark in July 1996. This initial and other subsequent asexual propagations conducted in controlled environments have demonstrated that the characteristics of 'Poulcot007' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcot007'. Specifically illustrated in the drawings:

FIG. 1.2; Flower bud at various stages of development;

FIG. 1.3; Detached sepals, pedicel, and reproductive flower parts;

FIG. 2.2; Open flower, viewed from above;

FIG. 2.3; Mature leaves;

FIG. 2.4; Juvenile and mature bare stems exhibiting thorns;

DETAILED DESCRIPTION OF THE VARIETY

Figure 1:
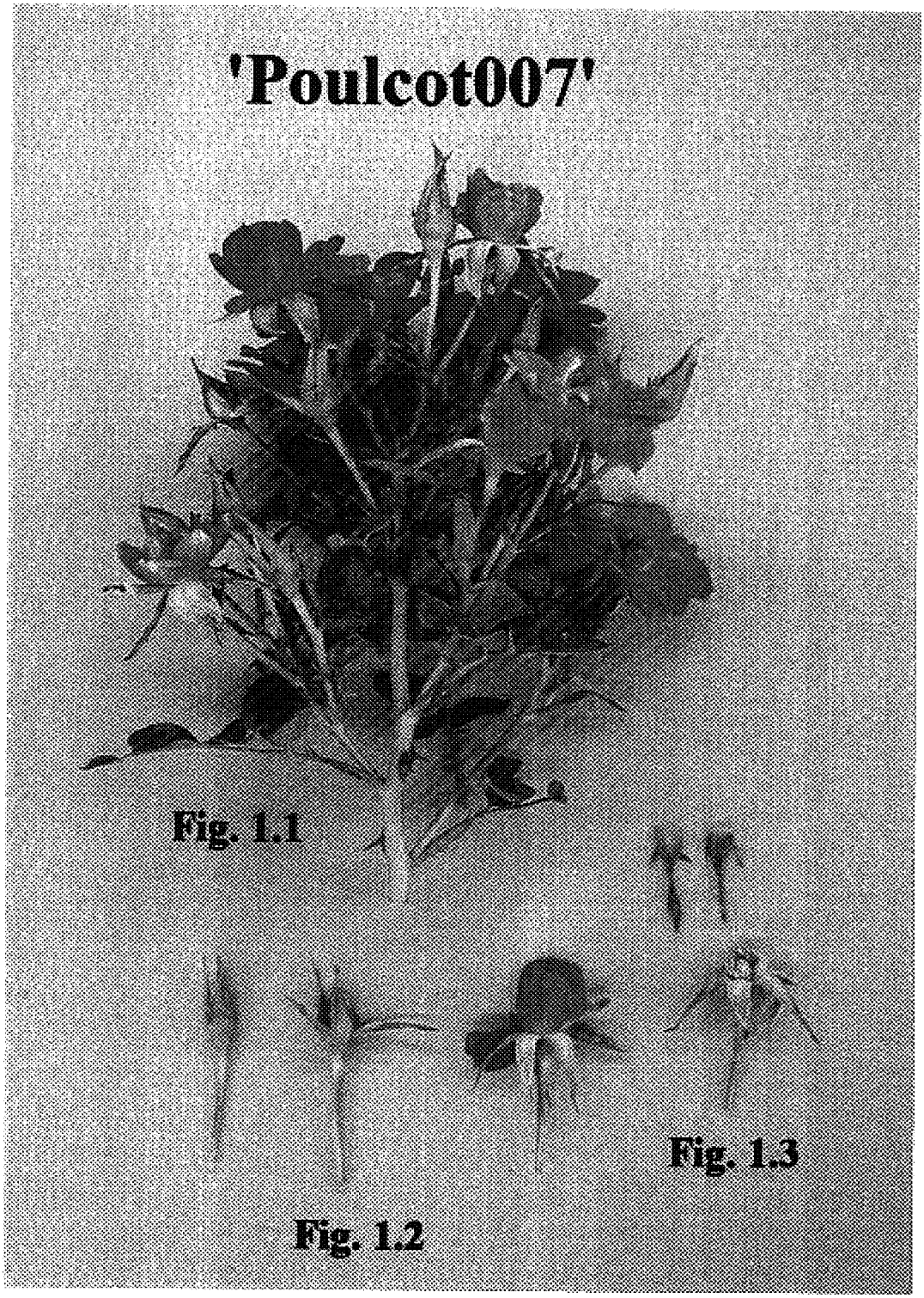
FIG. 1.1; Cluster of open flowers showing branching, and the attachment of leaves, buds, and peduncles.

The following is a description of 'Poulcot007', as observed in its growth in a field nursery in Jackson County, Oreg. Observed plants are 2 years of age, and were grown on *Rosa multiflora* understock. Color references are made using The Royal Horticultural Society (London, England)

Colour Chart, 2001, except where common terms of color are used.

For a comparison, several physical characteristics of the rose varieties 'Poulcot004', U.S. Plant patent application Ser. No. 11/001,947, and 'Poulcot006' U.S. Plant patent application Ser. No. 11/002,530 are compared to 'Poulcot007' in Chart 1.

CHART 1

| Characteristic | 'Poulcot007' | 'Poulcot004' | 'Poulcot006' |
|---|---|---|---|
| color of upper petal surface | Red 45B to 46C | Red-Purple 57A to 57B | Red-Purple Group 62A with intonations of Red-Purple Group 58B. |
| petal spot coloration | Yellow 4D | White 155B and Green-White 157A | Yellow 5B |
| petal dimensions | 18 to 23 mm long × 13 to 18 mm wide | 19 long × 15 mm wide | 26 long × 22 mm wide |

FLOWER AND FLOWER BUD

Blooming habit: Continuous.

Flower bud:

*Size.*—Upon opening, 15 mm in length from base of receptacle to end of bud. Bud diameter is 8 mm.

*Bud form.*—Ovate.

*Bud color.*—As sepals unfold, petals are Red Group 53B to 53C with intonations of Red Group 53A.

*Sepal inner surface.*—Color: Yellow-Green Group 146B and 146D. Anthocyanic pigments Greyed-Orange Group 166A to 166B. Surface: Medium pubescence observed.

*Sepal outer surface.*—Color: Yellow-Green Group 146B. Anthocyanic pigments Greyed-Orange Group 176A. Texture: Smooth with few stipitate glands.

*Sepal shape.*—Apex: Cirrhose. Base: Flat at union with receptacle.

*Sepal margin.*—Margins have medium foliaceous appendages on three of the five sepals. Stipitate glands observed in sparse quantities.

*Sepal size.*—21 mm (l)×7 mm (w).

*Receptacle.*—Texture: Smooth. Shape: Urn shaped to elliptical. Size: 5 mm (h)×3.5 mm (w). Color: Green Group 138A.

*Peduncle.*—Surface: Smooth with thorns. Color: Yellow Green Group 146B. Length: 8 to 12 cm. Diameter: 4.5 mm on average.

*Pedicel.*—Length: 25 to 30 mm on average. Diameter: 2 mm on average. Color: Yellow-Green Group 146C. Anthocyanic pigments Greyed-Orange Group 166B. Strength: Medium.

Flower bud development: Flower buds are borne in clusters of 5 to 11 flower buds. The inflorescence type is best characterized as a corymb.

Flower bloom:

*Fragrance.*—None.

*Duration.*—The blooms have a duration on the plant of approximately 6 to 9 days. Petals fall cleanly away from plant.

*Size.*—Flower diameter is 40 mm when open. Flower depth is 10 to 15 mm.

*Flower shape.*—Semi-double. When fully open flowers are nearly flat.

*Shape of flower, side view.*—Upon opening: Upper portion: Flattened convex. Lower portion: Flat. After opening: Upper portion: Flat. Lower portion: Flat.

*Petalage.*—Under normal conditions, flowers have 20 petals total, 8 to 10 of which are petaloids.

*Petal color.*—Upon opening, outer petals. Upper surface: Red Group 45B to 46C. Occasional weak petal streaking of Red-Purple Group 62A. Lower surface: Red Group 53C. Occasional petal streaking of Red Group 49A. Upon opening, inner petals. Upper surface: Red Group 45B to 46C. Occasional petal streaking of White Group 155B. Lower surface: Red Group 53C. Occasional streaking of White Group 155B. Basal petal spots, upon opening: Upper surface: Yellow Group 4D. Lower surface: Yellow Group 4D. After opening, outer petals. Upper surface: Red Group 45B to 46C. Occasional weak petal streaking of Red-Purple Group 62A. Lower surface: Red Group 53C. Occasional petal streaking of Red Group 49A. After opening, inner petals. Upper surface: Red Group 45B to 46C. Occasional petal streaking of White Group 155B. Lower surface: Red Group 53C. Occasional streaking of White Group 155B. After opening basal petal spots: Upper surface: Yellow Group 4D. Lower surface: Yellow Group 4D.

General tonality: On open flower Red Group 45B. After 6 to 7 days, changes in tonality are Red Group 45C to Red Group 53C.

Petals:

*Petal reflex.*—Flat.

*Margin.*—Entire, with point at the center of the apex.

*Shape.*—Generally, narrow elliptical. Apex: Cuspidate. Base: Acute.

*Size.*—18 to 23 mm (l)×13 to 18 mm (w).

*Texture.*—Smooth.

*Thickness.*—Medium.

Petaloids:

*Size.*—9 to 15 mm (l)×4 to 10 mm (w).

*Shape.*—Elliptical to asymmetrical.

*Color.*—Upper: Red Group 45B to 46C. With streaking of White Group 155B to Yellow Group 4C to 4D. Lower: Red Group 53C. With Streaking of White Group 155B and Red-Purple Group 62A.

Reproductive organs:

*Pollen.*—None observed.

*Anthers.*—Size: 2.5 mm in length. Color: Yellow Group 11A. Quantity: 85 to 95 average.

*Filaments.*—Color: Greyed-Orange Group 163B. Length: 4 mm.

*Pistils.*—Length: 4 to 5 mm. Quantity: 40 to 45.

*Stigmas.*—Level in location relative to the length of the filaments and the height of the anthers. Color: Orange-White Group 159B.

*Styles.*—Color: Red Group 46A.

*Hips.*—Color: Greyed-Orange Group 168B. Size: Typically 11 mm (l)×11 mm (w). Shape: Spherical.

PLANT

Plant growth: Moderately upright and spreading. When grown as a budded field grown plant on *Rosa multiflora* understock, the average height of the plant is 40 cm and the average width is 40 cm.

Stems:

*Color.*—Juvenile growth: Yellow-Green Group 146C. Anthocyanic intonations of Greyed-Red Group 181B. Mature growth: Yellow-Green Group 146C.

*Length.*—On average, canes are 25 to 30 cm from the base of the plant to the flowering portion.

*Diameter.*—9 mm.

*Internodes.*—On mature canes, there is an average distance of 20 mm between nodes.

*Surface texture.*—Young wood: Smooth. Older wood: Smooth.

Thorns:

*Incidence.*—13 thorns per 10 cm of stem on average.

*Size.*—8 mm.

*Shape.*—Upper side: Concave. Lower side: Deeply concave.

*Color.*—Juvenile thorns: Greyed-Red Group 181A. Mature thorns: Greyed-Yellow Group 161A to Yellow-Greyed Group 152C.

Plant foliage: Normal number of leaflets leaves in middle of the stem: 7 leaflets.

*Compound leaf.*—85 mm (l)×55 (w).

*Quantity.*—4 leaves per 10 cm of stem on average.

*Color of mature foliage.*—Upper side: Yellow-Green Group 147A. Lower side: Yellow-Green Group 147B.

Plants leaves and leaflets:

*Stipules.*—Size: 16 mm in length. Shape: Linear, slightly broad based with outward extending apecies. Margins: Serrated with stipitate glands. Quantity: 2 per compound leaf.

*Petiole.*—Length: 20 mm. Diameter: 2 mm.

*Upper surface.*—Color: Yellow-Green Group 147A. Observations: Few stipitate glands.

Lower surface: Color: Yellow-Green Group 146C.

*Rachis.*—Length: 30 mm. Upper surface: Color: Yellow-Green Group 147A. Observations: Few stipitate glands. Lower surface: Color: Yellow-Green Group 146C. Observations: Few small prickles.

*Leaflet.*—Edge: Serrated. Size: Average size of the terminal leaflet on normal leaves is 31 mm (1)×18 mm (w). Shape: Elliptical. Base: Obtuse. Apex: Acuminate. Texture: Smooth. Thickness: Average. Arrangement: Odd pinnate. Venation: Reticulate. Glossiness: Matte.

Disease resistance: Above average resistance to mildew, rust, black spot, and Botrytis under normal growing conditions in Jackson County, Oreg.

Cold hardiness: The variety 'Poulcot007' has been found to be cold tolerant to USDA Cold Hardiness Zone 6.

Heat tolerance: The new variety has been found to be tolerant of growing conditions described in the American Horticulture Society heat zone map, zone 7.

It is claimed:

1. A new and distinct variety of rose plant of the shrub rose class named 'Poulcot007', illustrated and described herein as a distinct and novel rose variety due to its abundant medium red flowers, disease resistance and extended period of bloom.

* * * * *

'Poulcot007'
Fig. 1.1
Fig. 1.3
Fig. 1.2

Figure 2:
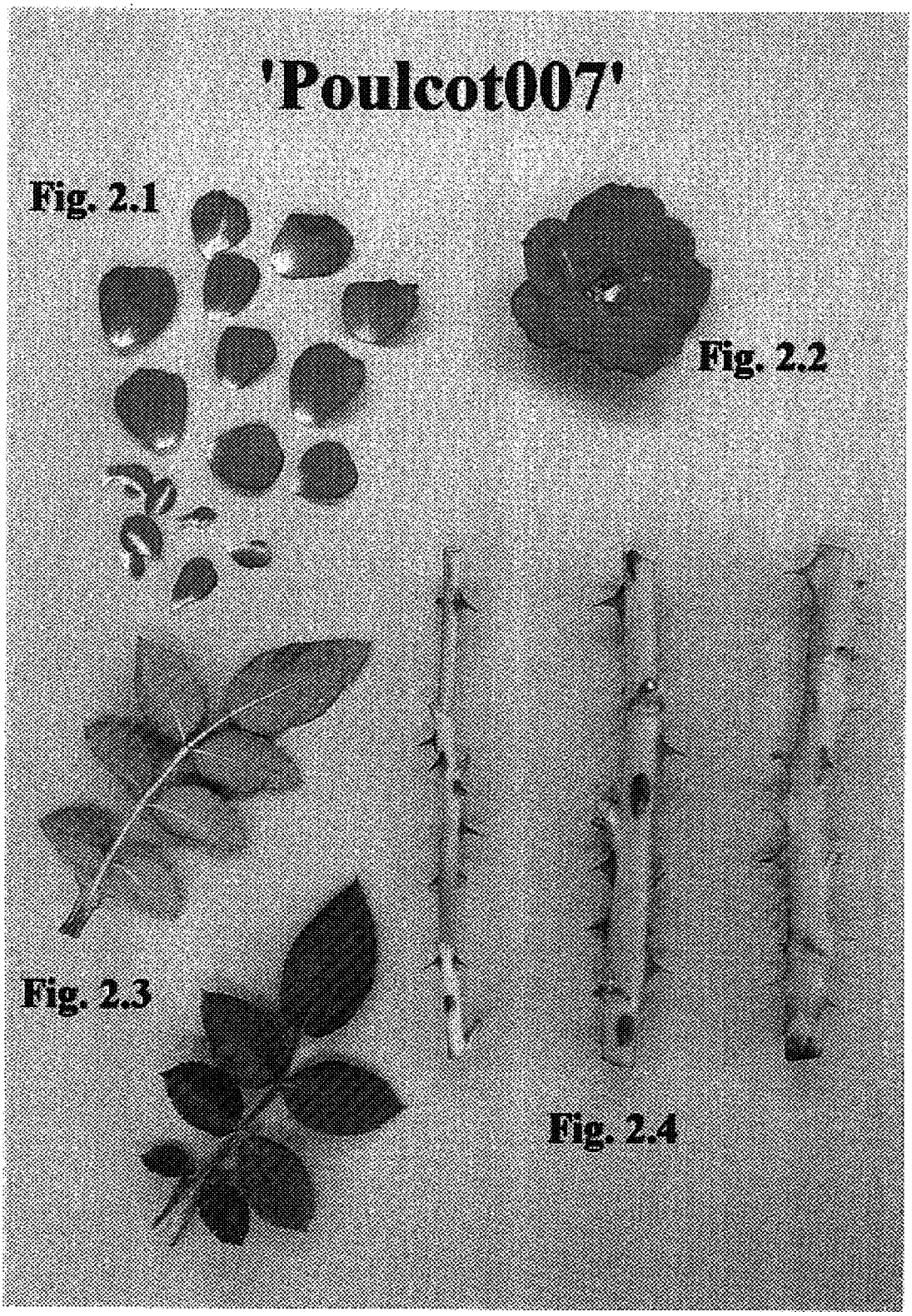
FIG. 2.1; Flower petals, detached.
Figure 3:
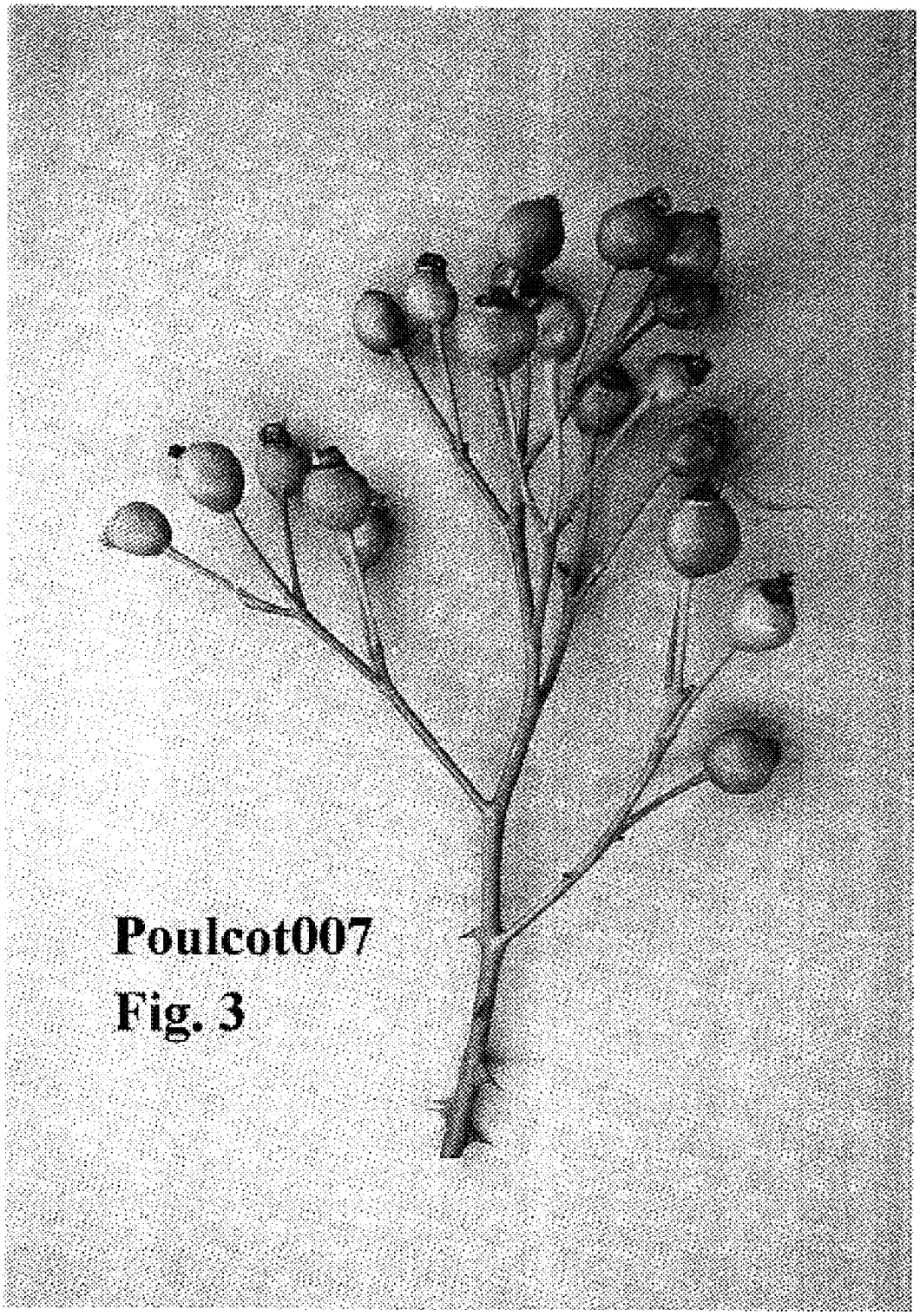
FIG. 3; Rose hips.

'Poulcot007'
Fig. 2.1
Fig. 2.2
Fig. 2.3
Fig. 2.4